(12) United States Patent
Marcussen

(10) Patent No.: US 8,080,703 B2
(45) Date of Patent: Dec. 20, 2011

(54) DRESSING

(75) Inventor: Jan Marcussen, Taastrup (DK)

(73) Assignee: Coloplast A/S, Humlebaek (DK)

( * ) Notice: Subject to any disclaimer, the term of this patent is extended or adjusted under 35 U.S.C. 154(b) by 57 days.

(21) Appl. No.: 10/536,422

(22) PCT Filed: Nov. 25, 2003

(86) PCT No.: PCT/DK03/00806
§ 371 (c)(1),
(2), (4) Date: May 26, 2005

(87) PCT Pub. No.: WO2004/047695
PCT Pub. Date: Jun. 10, 2004

(65) Prior Publication Data
US 2006/0064049 A1    Mar. 23, 2006

(30) Foreign Application Priority Data

Nov. 26, 2002  (DK) .................................. 2002 01824

(51) Int. Cl.
| A61B 17/00 | (2006.01) |
| A61F 13/00 | (2006.01) |
| A61F 13/02 | (2006.01) |
| A01N 25/34 | (2006.01) |
| A61K 9/70  | (2006.01) |
| A61L 15/00 | (2006.01) |
| A61L 15/16 | (2006.01) |

(52) U.S. Cl. ................ 602/55; 602/41; 602/42; 602/43; 602/54; 602/58; 128/887; 128/888; 424/402; 424/443; 424/445; 424/447; 424/448

(58) Field of Classification Search .................. 128/155, 128/158, 887–889; 602/58, 55, 40–43; 424/402, 424/443, 445, 447, 448
See application file for complete search history.

(56) References Cited

U.S. PATENT DOCUMENTS

| 3,835,992 | A | * | 9/1974 | Adams, IV .................... 206/390 |
| 4,231,369 | A |   | 11/1980 | Sorensen et al. |
| 4,260,443 | A | * | 4/1981 | Lindsay et al. ............... 156/220 |
| 4,367,732 | A |   | 1/1983 | Poulsen et al. |

(Continued)

FOREIGN PATENT DOCUMENTS

| CA | 2 060 702 | 8/1992 |

(Continued)

*Primary Examiner* — Patricia Bianco
*Assistant Examiner* — Brandon Jackson
(74) *Attorney, Agent, or Firm* — Coloplast Corp., Coloplast A/S; Daniel G. Chapik; Nicholas R. Baumann

(57) ABSTRACT

A dressing able to adhere to the skin and/or a wound for covering a portion of the anatomical surface of a living being and demonstrating considerably increased wearing time. The dressing has a backing layer and a layer of skin-friendly adhesive for adhering to the skin, and includes a pattern of connected indentations formed in a pattern that is not linear and which progresses in at least three main directions.

17 Claims, 5 Drawing Sheets

U.S. PATENT DOCUMENTS

| | | | |
|---|---|---|---|
| 4,798,604 A | | 1/1989 | Carter |
| 4,867,748 A | | 9/1989 | Samuelsen |
| 4,990,144 A | | 2/1991 | Blott |
| 5,012,801 A | | 5/1991 | Feret |
| 5,133,821 A | * | 7/1992 | Jensen .................. 156/245 |
| 5,328,450 A | * | 7/1994 | Smith et al. ............. 602/59 |
| 5,356,372 A | | 10/1994 | Donovan et al. |
| 5,486,158 A | * | 1/1996 | Samuelsen .............. 602/46 |
| 5,505,720 A | * | 4/1996 | Walters et al. .......... 604/378 |
| 5,633,007 A | * | 5/1997 | Webb et al. ............. 424/443 |
| 5,643,187 A | | 7/1997 | Næstoft et al. |
| 5,704,905 A | * | 1/1998 | Jensen et al. ........... 602/58 |
| 5,714,225 A | | 2/1998 | Hansen et al. |
| 5,782,787 A | * | 7/1998 | Webster ................. 602/46 |
| 5,902,260 A | * | 5/1999 | Gilman et al. ........... 602/57 |
| 6,713,659 B2 | * | 3/2004 | Bodenschatz et al. ..... 602/56 |
| 6,969,548 B1 | * | 11/2005 | Goldfine ............... 428/159 |

FOREIGN PATENT DOCUMENTS

| | | |
|---|---|---|
| DE | 42 03 130 A1 | 8/1992 |
| EP | 0 256 893 | 2/1988 |
| EP | 0 409 587 | 1/1991 |
| EP | 0 573 708 A1 | 12/1993 |
| EP | 0 768 071 A1 | 4/1997 |
| GB | 1075939 | 7/1967 |
| GB | 2 276 087 | 9/1994 |
| JP | 2002-035196 | 2/2002 |
| WO | WO 90/10424 | 9/1990 |
| WO | WO 91/10415 | 7/1991 |
| WO | WO 93/00056 | 1/1993 |
| WO | WO 99/36017 | 7/1999 |

* cited by examiner

Out of scale

A-A
Out of scale

DRESSING

This is a nationalization of PCT/DK03/000806 filed Nov. 25, 2003 and published in English.

BACKGROUND OF THE INVENTION

1. Field of the Invention

The present invention relates to dressings, in particular dressings for covering a portion of the anatomical surface of a living being, a method for preparing such dressings, and a method of treating a portion of the anatomical surface of a living being, especially a joint or a protruding part of the body.

2. Description of the Related Art

Conventionally, dressings for the treatment or prevention of wounds or pressure sores or even unbroken skin are essentially flat dressings, which are sufficiently mouldable to be applied to flat or slightly curved areas of the body. Such flat dressings are not very suitable for applying on protruding parts of the body or joints e.g. heels or especially elbows or knees having not only a very pronounced curvature but also being subject to constant bending which often causes wrinkling and focusing of stresses in the dressing often causing slipping of the adhesive and unintended detachment of the dressing.

WO 93/00056 discloses that a skin-friendly dressing having grooves or ditches surrounding a central part of the dressing has a high degree of flexibility. The ditches are surrounding a central part of the adhesive.

EP patent No. 0 768 071 discloses a wound dressing especially for use in the sacrum area, said dressing having one or more linear depressions that assist a user in applying, flexing or folding the dressing and that the dressing may have two sets of spaced parallel depressions forming a grid which is useful in the wound assessment. The thickness of the adhesive layer at the base of the depressions should at least be as great as the thickness of the border portion of the adhesive layer.

GB patent No. 1,075,939 discloses an adhesive bandage having a thermoplastic top film provided with embossments in order to allow passage of water vapour though the film.

Published EP patent application No. 0 256 893 discloses a non-adherent dressing comprising a film which contains depressions over the wound contacting area which depressions contain a viscous pharmaceutical composition which is suitable for topical application. The depressions may be in the form of a pattern of conical depressions.

GB patent No. 1,075,939 and EP patent application No. 0 256 893 are silent with respect to flexibility.

WO 99/36017 discloses a dressing comprising a substantially water-impervious layer and a skin-friendly adhesive having a pattern of indentations, which diminishes or disappears when the dressing is moisturised. The grooves are stated to have a depth of at least 25% and more preferred at least 50% of the thickness of the dressing and it is stated that the pattern may increase the flexibility of the dressing.

U.S. Pat. No. 5,356,372 discloses an occlusive pressure-reducing wound dressing consisting of an occlusive wound contacting layer and a pressure-reducing layer and it is claimed that the pressure-reducing layer has a contour for adapting to curved body surfaces. Thus, the top surface comprises a plurality of elevated domains and lowered domains providing a lower overall resistance to larger applied compressive force. However, the lowered domains between the elevated domains provide valleys extending across the pressure-reducing layer in substantially right-angled relationship to each other so that the bending of the relatively thick foam in a multiplicity of directions is facilitated.

DE 42 03 130 discloses a medical dressing, the surface of which in certain areas has been embossed so that the embossed areas are transparent. The embossed fraction of the dressing is greater than 20% of the surface for enabling a sufficient transparency to inspect the below wound and skin. DE 42 03 130 shows different embossment patterns all showing linear indentations progressing in several directions and is silent with respect to the disadvantages of such lines.

None of the above-referenced publications address the problems associated with application of dressings on protruding parts of the body such as joints e.g. heels or especially elbows or knees having not only a very pronounced curvature but also being subject to constant bending ensuring a snug fit and a safe grip and at the same time avoiding focusing of stress along lines of the indentations for avoiding formation of wrinkles or folds during application which may lead to edges not being smooth and forming points open to initiation of rolling-up or peeling of the dressing from the skin or leave a part of the edge open for attack by moisture, altogether causing a reduction of the wear time of the dressing as compared to the theoretically expected wear time of the dressing before it should be replaced.

Furthermore, it has been found that the flexibility of a dressing is important, with respect to the shape, the size and the adhesive of the dressing, not only in use but also during the application. When applying a dressing on a part of the body that is frequently bent such as the inner or outer side of a joint or inside a hand, or a protruding part of the body or a part of the body having a double curvature such as the inter digital area flexibility is a very important property as the dressing must be able to adapt to the contour of the skin surface and to follow movements without slipping the skin or exposing the skin to significant stress causing pain or unpleasant feeling and during use a sufficient flexibility enabling the dressing to follow the movement of the underlying skin is decisive for obtaining a long wear time and for reducing the risk of migration of humidity from a wound or an abrasion to neighbouring areas which may cause maceration of the skin or leakage at the edge of the dressing.

It has now been found that the wear time of dressings applied to a part of the body that is frequently bent or a part of the body having a double curvature or protruding parts of the body especially heels, knuckles, elbows or knees, the inner part of the hand or e.g. the inter digital area may be increased considerably by using a dressing of the present invention fulfilling the above-mentioned demands.

SUMMARY OF THE INVENTION

The present invention relates to a dressing for covering a portion of the anatomical surface of a living being, said dressing being able to adhere to the skin, and/or a wound, said dressing comprising a backing layer and a layer of a skin-friendly adhesive for adhering to the skin, and said dressing having a pattern of indentations.

The invention also relates to a method for preparing a dressing comprising a backing layer and a layer of a skin-friendly adhesive for adhering to the skin, which dressing has a pattern of indentations.

Furthermore, the invention relates to a method of treating a portion of the anatomical surface of a living being, especially a protruding part of the body.

BRIEF DESCRIPTION OF THE DRAWINGS

The invention is disclosed more in detail with reference to the drawings in which.

DETAILED DESCRIPTION OF THE PRESENT INVENTION

Figure 1:
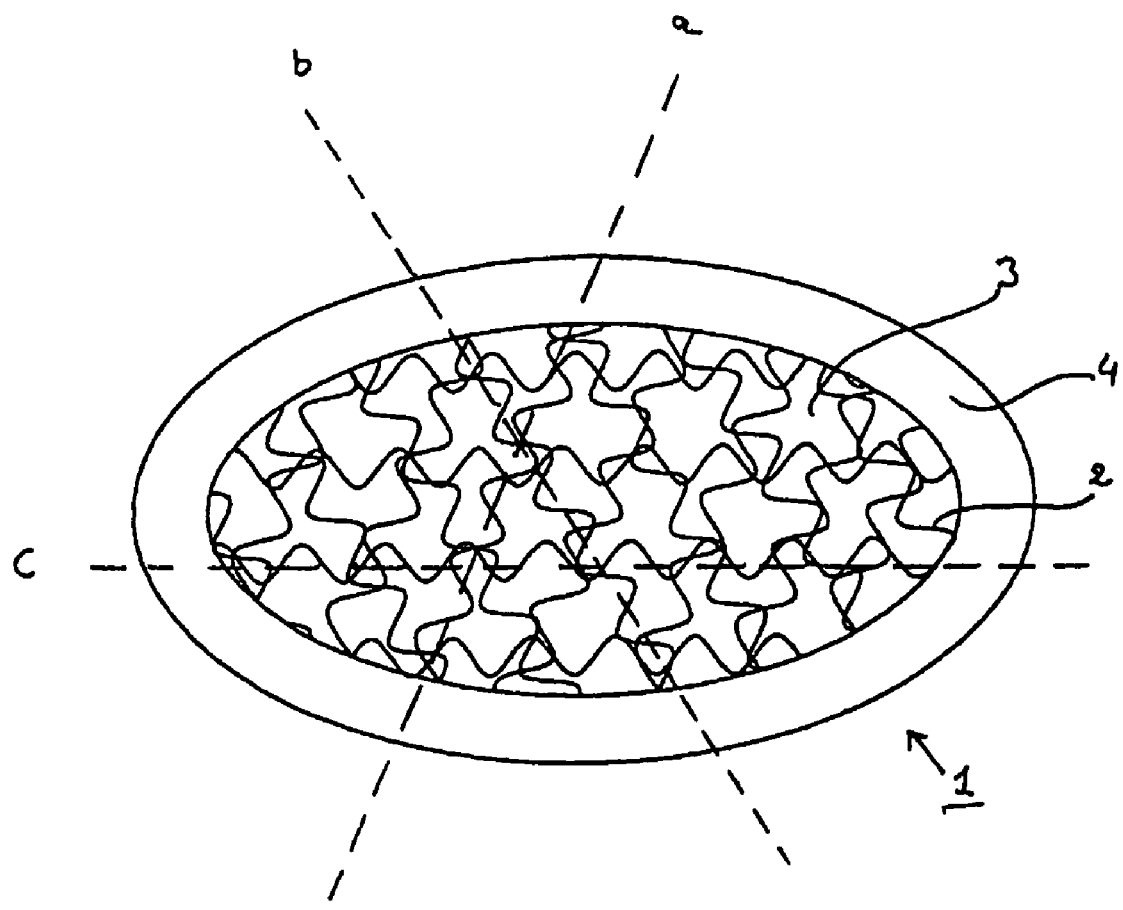
FIG. 1 shows a top view of an embodiment of a dressing of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention relates to a dressing for covering a portion of the anatomical surface of a living being, said dressing being able to adhere to the skin, and/or a wound, said dressing comprising a backing layer and a layer of a skin-friendly adhesive for adhering to the skin, and said dressing having a pattern of indentations wherein the indentations are in the form of a pattern of connected indentations not being linear and progressing in at least three main directions.

The pattern of indentations of a dressing according to the present invention covers all the central surface of the dressing providing flexibility to all of the surface of the dressing and not only to the distal part thereof.

The dressing of the invention is suitable for covering blisters, cuts, graces and abrasions and other skin injuries especially on a part of the body that is frequently bent such as a joint, e.g. heels, knuckles, elbows or knees, or inside a hand, on a protruding part of the body such as the tip of a finger or toe, or on a part of the body having a double curvature such as the inter digital area or other parts of the body that are stressed by movements as it has a high capability of adapting to the specific site during application and then, when applied, a high capability of following movements of the skin like a second skin. Thus, the risk of migration of humidity from a wound or an abrasion to neighbouring areas causing maceration is better prevented.

A dressing of the invention is preferably large enough to cover abrasions on both knees and elbows, large enough to anchor well at both or several sides of the joint, and yet preferably small enough to be applied with one hand when applying on an elbow.

Furthermore, it has been found that the pattern of indentations progressing in at least three directions allows maximum flexibility and it allows the dressing to bend in the pattern of indentations without introducing stress to the adhesive material and reducing the risk of peeling of the dressing from the skin. The effect is believed to be supported by the non-linearity and number of the indentations, which distributes the stress introduced when bending and stretching a joint rather than focussing the stress along the edge or rectilinear indentations, which might initiate formation of a fold or peeling of the dressing.

It has been found that the wearing time of dressings of the invention applied to protruding parts of the body, especially the elbow and knee joints is increased considerably, typically by far more than 50% and in many cases by several hundred percent which is presumed to be ascribed partly to the great degree of flexibility of the dressings of the invention due to the presence of indentations progressing in at least three main directions and partly to the reduced risk of proceeding of wrinkles or beginning peeling of the dressing from the edge to the centre of the dressing. Thus, it has been found that on joints or protruding parts of the body, a pattern that allows the dressing to bend in at least three directions, and more preferably in six or more directions, shows considerably prolonged wear time.

It is preferred that the indentations are in the form of a symmetrical pattern providing a more controlled spacing of the general directions of progression of the indentations.

In accordance with an especially preferred embodiment of the invention, the indentations are in the form of a honeycomb pattern in which the indentations are relatively narrow grooves defining a pattern of adhesive areas having the maximum thickness of the dressing and being of essentially hexagonal shape. The angled propagation of the indentations is believed to distribute the stress rather than to focus the same and thus to prevent formation of folds which might open for peeling of the dressing at the edge or expose the adhesive and cause adhesion to e.g. clothes.

It is believed that the high flexibility is achieved as a consequence of the combination of the size of the parts of the pattern, i.e. separate hexagonal shape of the adhesive areas between the indentations, the distance between the separate pattern parts, the thickness of the overall adhesive layer and the thickness of the adhesive layer in the pattern.

It has been found suitable when the distance between the areas between the indentations, i.e. the width of the indentations, is in the magnitude of from about 0.2 to about 3 millimeters, e.g. 0.5-2 millimeters, suitably 1.2 millimeters providing a suitable flexibility. Furthermore, it has been found to provide a suitable flexibility when the size of the adhesive areas between the indentations is from 2 to 25 millimeters, more preferred from 2 to 16 millimeters and preferably from 2 to 12 millimeters. It is to be taken into account when designing the shape and width of the indentations that the pattern of indentations progressing in at least three directions should not provide any lines of sight across the dressing in any direction for avoiding focussing of stress along such lines of the indentations. In a preferred embodiment of the invention, the total area of the indentations is below 20% of the total surface of the dressing, suitably below 18% providing a sufficient flexibility combined with high security against formation of wrinkles or leakages. For improving the flexibility of the dressing it is preferred to provide indentations being wider at the top end and narrower at the bottom e.g. having a trapezoidal cross-section. This is especially suitable when the dressing is to be used at the palm or the inner side of a joint such as the elbow or the knee, (the popliteral space of the knee or the cubital area of the elbow) as it provides a better flexibility when the hand is closed or an elbow or a knee is bent.

In another preferred embodiment of the invention, the indentations are in the form of a pattern in which the indentations are relatively thin grooves defining a pattern of adhesive areas having the maximum thickness of the dressing and being of essentially circular shape.

The indentations are suitably made from the side of the backing layer in which case it is simple to add a step for effecting the impression in a conventional line for producing medical dressings. Furthermore, this embodiment provides an uninterrupted adhesive surface facing the skin to be covered which is pertinent for obtaining a protection against migration of humidity from a wound or an abrasion to neighbouring parts of the skin or to the edge of the dressing. Still further, an uninterrupted adhesive surface facing the skin will not give rise to unpleasant feeling during physical activity due to "opening and closing" of the indentations which may cause pinching or pain.

In order to ensure a suitable flexibility of the dressing it is preferred that the indentations have depth of at least two thirds of the total thickness of the dressing. In accordance with a preferred embodiment the indentations have depth of at least 75% of the total thickness of the dressing, more preferred up to 90% and even exceeding 90% of the total thickness of the dressing. Thus, the dressing may be considered as a number of thick parts connected by thinner bridging parts. The bridging parts are preferably sufficiently large and present in a sufficient number to allow stress originated from movement of an elbow or knee joint to be relaxed without proceeding from one thick part to the next. It is preferred that the thickness of the dressing at the bottom of the indentations of a dressing of the invention is below 0.5 millimetres e.g. from 0.05 to 0.4 millimetres, suitably form 0.1 to 0.3 millimetres providing a suitable flexibility.

It is believed that the advantages obtained are greater when having relatively deep indentations as deep pattern will divide the dressing into isolated zones and that this will prevent the dressing from peeling off due to "rolling-up" at the edge. Normally, once rolling-up at the edge of a conventional dressing starts, there is nothing to prevent further peeling of the whole dressing. On the contrary, a dressing of the invention is provided with zones of small thickness stopping the propagation of the peeling and enabling cutting off a part of the edge along the indentations.

Still further, it is believed that pattern may also offer further advantages as the zones will prevent/slow down the propagation of swelling of a hydrocolloid from to reach the whole dressing, and to reach the edge and cause slip of the dressing, and also provide an additional stability and comfort due to the discontinuous attachment to the skin surface.

The dressing of the invention is especially suitable for use on hands or feet or on a joint such as a heel, a knee, an elbow, or a knuckle, preferably a knee, an elbow, or a knuckle.

It is suitable that the backing layer is a substantially water-impervious film which protects the adhesive from being adversely affected when the wearer is bathing or in case of incidental wetting of the area and especially when the adhesive is water absorbing.

In accordance with a preferred embodiment the backing layer is a film showing a low surface friction for reducing the stress transferred to the skin due to physical activity of the user as a dressing covered by clothing will move relatively to the dressing. Such stress may cause a rolling up of the edge or even slippage of the grip between the dressing and the skin reducing the wear time.

It is preferred that a border zone of the dressing is free of indentations for providing a sealing preventing e.g. dust and infectious matter from entering an injured part of the skin covered by the dressing.

The outer periphery of the dressing is preferably bevelled in analogy with the disclosure of U.S. Pat. No. 4,867,748 or U.S. Pat. No. 5,133,821 in order to reduce the risk of "rolling-up" the edge of the dressing reducing the wear-time. The edge is preferably bevelled so that the thickness adjacent to the edge does not exceed about 30% of the maximum thickness of the dressing, more preferred not exceeding 25% of the maximum thickness for dressings having a maximum thickness above about 0.7 millimetres, whereas the thickness adjacent to the edge for dressings having a maximum thickness below about 0.5 millimetres preferably does not exceed about 50% of the maximum thickness of the dressing.

It is preferred that the thickness of the adhesive in the bottom of the pattern of indentations is less than the thickness of the beveled edge which provides for a very flexible area for contacting the protruding part of the body.

The dressing of the invention may be in one embodiment of the invention in the form of individual dressings as indicated above having a bevelled edge. In accordance with another embodiment of the invention, the dressing is in the form of a long strip of dressing having bevelled edges. This embodiment is suitable for tailoring individual dressings by cutting a suitable length of the strip. It is preferred to cut in the bottom of the indentations, as a tailored dressing having relatively thin edges reducing the risk of "rolling-up" of the edge is then obtained. It is also considered an aspect of the invention to provide a series of dressings in the form of a long strip of dressing having bevelled edges and having a pattern of connected indentations not being linear and progressing in at least three different main directions in which some of the indentations are broader than the remaining indentations as stated above, e.g. up to about 5 millimeters and providing a pattern for allowing a custom adaptation of a dressing to a specific area without losing the effect of a bevelled edge by providing an edge area having a sufficient flexibility. Such broader indentations may in accordance with a further embodiment of the invention be applied to individual dressings for enabling a custom cutting of the dressing to the specific site where the dressing is to be used. The broader indentations may thus e.g. follow the outer contour of the dressing, enabling a reduction of the size of the dressing without losing the advantage of a predetermined shape such as a "banana"-shape.

The invention furthermore relates in a further aspect to a method for preparing a dressing comprising a backing layer and a skin-friendly adhesive for adhering to the skin and a backing layer, which dressing has a pattern of indentations not being linear and progressing in at least three main directions. The method includes providing a supply of dressing having a backing layer and a layer of skin friendly adhesive, placing the dressing in a press together with a mould having a surface corresponding to the desired pattern of indentations and providing a sufficient pressure to provide the desired pattern of indentations. The method of the invention may be carried out in a conventional stepwise manner or the mould may have a continuous surface corresponding to the desired pattern of indentations for producing individual dressings or dressings in the form of a continuous long strip of dressings as described above. A mould having a continuous surface may e.g. be located on a roller in a manner known per se.

In a third aspect the invention relates to a method of treating a portion of the anatomical surface of a living being comprising applying a dressing for covering the portion of the anatomical surface of a living being, said dressing being able to adhere to the skin of a living being and said dressing comprising a backing layer and a skin-friendly adhesive, which dressing comprises a pattern of indentations wherein the indentations are in the form of a pattern of connected indentations not being linear and progressing in at least three main directions.

A dressing of the invention may preferably be sterilised for avoiding the risk of causing infections when applied to skin areas having broken skin.

It is not critical whether or not the dressing is sterilised, if the dressing is applied to non-broken skin, e.g. on an elbow for preventing and protecting against abrasion which is also considered an aspect of the present invention.

The skin-friendly adhesive may be any skin-friendly adhesive known per se for production of medical articles, which are to be adhered to human skin, preferably an adhesive comprising hydrocolloids or other moisture absorbing constituents for prolonging the time of use. The adhesive may suitably be of the type disclosed in U.S. Pat. Nos. 4,231,369, 4,367,732, 4,867,748, and 5,714,225. Especially preferred are the adhesives disclosed in U.S. Pat. Nos. 4,367,732, and 5,714,225.

The dressing of the invention may in one embodiment of the invention be in the form of a mono-phase adhesive, i.e. made from one adhesive component or in accordance with another embodiment of the invention be in the form of a two-zone adhesive, e.g. of the general type disclosed in U.S. Pat. No. 5,714,225, i.e. a part of or all of the adhesive areas of the dressing having maximum thickness being constituted by more than one type of adhesive.

A water impervious layer or film may be of any suitable material known per se for use in the preparation of wound dressings e.g. a foam, a non-woven layer or a polyurethane, polyethylene, polyester or polyamide film. In accordance with the invention it has been found in practice that with the use of a thinner backing layer or film than is normally used when preparing medical dressings, an improved stretchability and adaptability is obtained at the same time as the modulus is reduced. These properties are obtained using the same load of adhesive as is conventionally used, and thus, the conventional properties of the adhesive are retained as opposed to the case in which the load of adhesive was lowered giving a risk of insufficient tack and adhesive properties.

The water impervious layer or film is preferably a low-friction flexible polymer film reducing the risk of unwanted stress in the area of the crack impeding the healing of a crack on a very exposed site. A suitable material for use as water impervious layer is a film conventionally used as backing layer in the preparation of wound dressings, suitably having a thickness of about 30 microns.

An especially suitable material for use as a water impervious film is a polyurethane film. A preferred low friction film material is disclosed in U.S. Pat. No. 5,643,187.

A preferred thickness of this film may be below 20 microns, more preferred about 12-18 microns, e.g. about 15 microns, thus resulting in a significant decrease of the modulus, compared to a film that is normally used when preparing medical dressings. An improved stretchability and adaptability is obtained at the same time as the modulus is reduced. The thickness of the film must be chosen in consideration of the pressure used in the production process in order to avoid a rupture of the film along the indentations when removing the dressing.

A dressing of the invention is optionally covered in part or fully by one or more release liners or cover films to be removed before or during application.

A protective cover or release liner may for instance be siliconized paper. It does not need to have the same contour as the dressing, e.g. a number of dressings may be attached to a larger sheet of protective cover. The protective cover is not present during the use of the dressing of the invention and is therefore not an essential part of the invention.

Furthermore, the dressing of the invention may comprise one or more "non touch" grip(s) known per se for applying the dressing to the skin without touching the adhesive layer. Such a non-touch grip is not present after application of the dressing. For larger dressings it is suitable to have 2 or 3 or even 4 "non-touch" grips.

It is advantageous to provide a dressing of the invention with components for treatment or prophylaxis of formation of wounds and/or skin abnormalities, e.g. with emollients or an active constituent e.g. retinoids for treating or preventing formation of psoriasis, eczema, callous skin, corns, insect bites, acne or blisters. The dressing of the invention may also contain medicaments such as bacteriostatic or bactericide compounds, e.g. iodine, iodopovidone complexes, chloramine, chlorohexidine, silver salts, zinc or salts thereof, tissue-healing enhancing agents, e.g. RGD tripeptides and the like, enzymes for cleansing of wounds, e.g. pepsin, trypsin and the like, pain relieving agents, or agents having a cooling effect which is also considered an aspect of the invention. Such agents are preferably enclosed in a part of the adhesive.

DESCRIPTION OF THE PREFERRED EMBODIMENTS

The invention is now explained more in detail with reference to the drawings showing preferred embodiments of the invention.

Reference is made to FIG. 1 which shows a top view of an embodiment of a dressing 1 of the invention, said dressing being able to adhere to the skin, and/or a wound on a protruding part of the body, said dressing comprising a backing layer 2 and a layer of a skin-friendly adhesive for adhering to the skin and a backing layer, said dressing having a pattern 3 of indentations progressing in three main directions a, b, and c wherein the indentations are in the form of a pattern of connected indentations in the form of sinuidal indentations progressing in at least three main directions. The dressing has a border zone 4 being free of indentations.

Figures 2, 3:
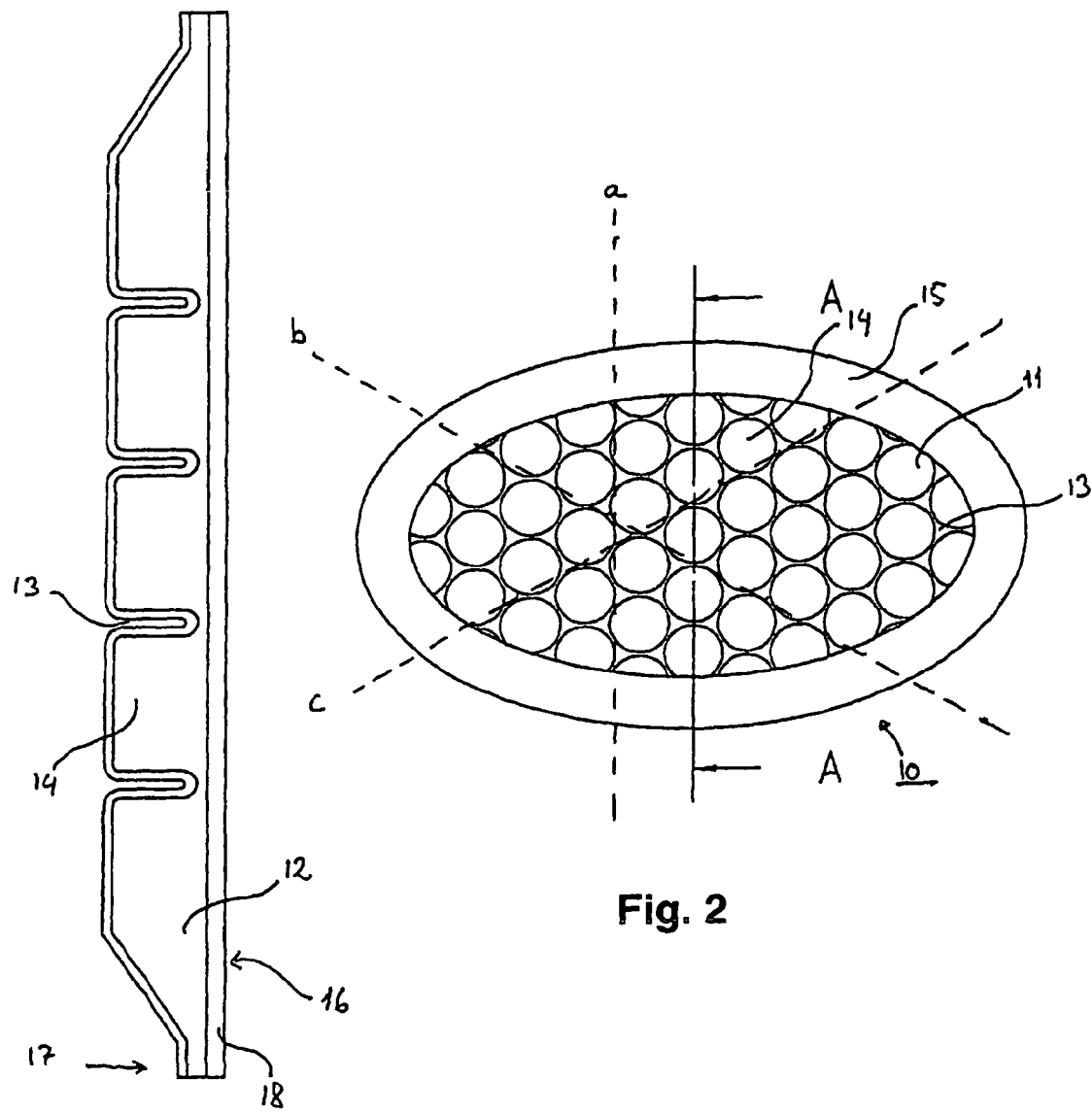
FIG. 2 shows a top view of another embodiment of a dressing of the invention.
FIG. 3 shows in an enlarged scale a sectional view of the embodiment of FIG. 2 along the line A-A.

FIG. 2 shows a top view of another embodiment of a dressing 10 of the invention, said dressing being able to adhere to the skin, and/or a wound on a protruding part of the body, said dressing comprising a backing layer 11 and a layer 12 of a skin-friendly adhesive for adhering to the skin and a backing layer, said dressing having a pattern 13 of indentations progressing in three main directions a, b, and c wherein the indentations are in the form of a pattern of connected indentations defining a pattern of adhesive areas 14 having the maximum thickness of the dressing and being of essentially circular shape. The dressing has a border zone 15 being free of indentations.

FIG. 3 shows in an enlarged scale a sectional view of the embodiment of FIG. 2 along the line A-A, and more clearly showing the adhesive areas 14 having the maximum thickness of the dressing and the indentations 13. Furthermore, the rim 16 is shown having a bevel leaving a relatively thin edge 17. Furthermore, the top film layer 11 is shown as well as a release liner 18.

Figure 4:
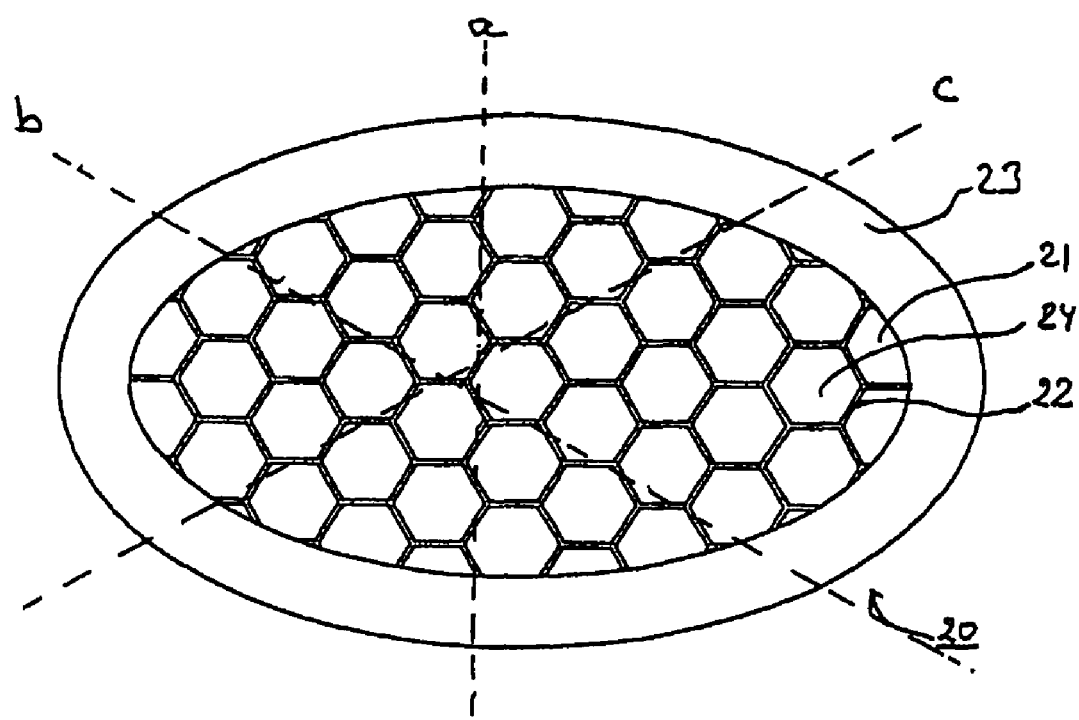
FIG. 4 shows a top view of a further embodiment of a dressing of the invention.

FIG. 4 shows a top view of a further and preferred embodiment of a dressing 20 of the invention said dressing being able to adhere to the skin, and/or a wound on a protruding part of the body, said dressing comprising a backing layer 21 and a layer of a skin-friendly adhesive for adhering to the skin and a backing layer, said dressing having a pattern 22 of indentations wherein the indentations are in the form of a pattern of connected indentations progressing in three main directions a, b, and c defining a pattern of adhesive areas 24 having the maximum thickness of the dressing and being of essentially hexagonal shape. The dressing has a border zone 23 being free of indentations.

Figure 5:
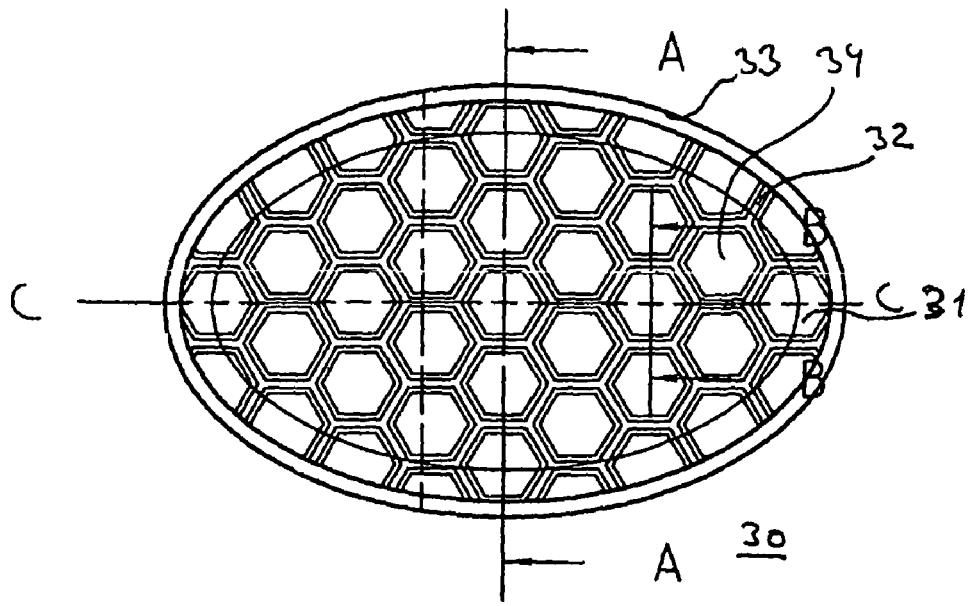
FIG. 5 shows a top view of a still further embodiment of a dressing of the invention.

FIG. 5 shows a top view of a another preferred embodiment of a dressing 30 of the invention said dressing being able to adhere to the skin, and/or a wound on a protruding part of the body, said dressing comprising a backing layer 31 and a layer of a skin-friendly adhesive for adhering to the skin and a backing layer, said dressing having a pattern 32 of indentations wherein the indentations are in the form of a pattern of connected indentations progressing in three main directions, a pattern of adhesive areas 34 having the maximum thickness of the dressing and being of essentially hexagonal shape. The dressing has a border zone 33 being free of indentations.

Figure 6:
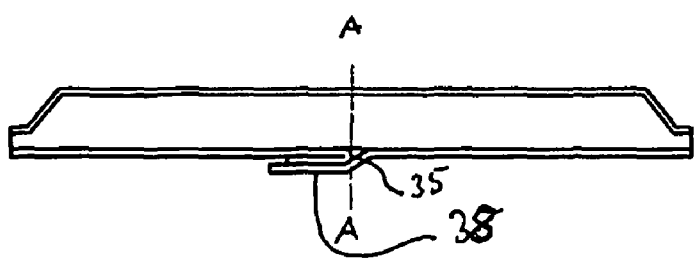
FIG. 6 shows the localisation of a release liner with respect to the Section A-A in FIG. 5.

FIG. 6 shows schematically a section of the embodiment of FIG. 5 along the line C-C showing the release liner and a fold 35 of a non-touch feature allowing gripping and removing the release liner 38 without touching the adhesive surface.

Figure 7:
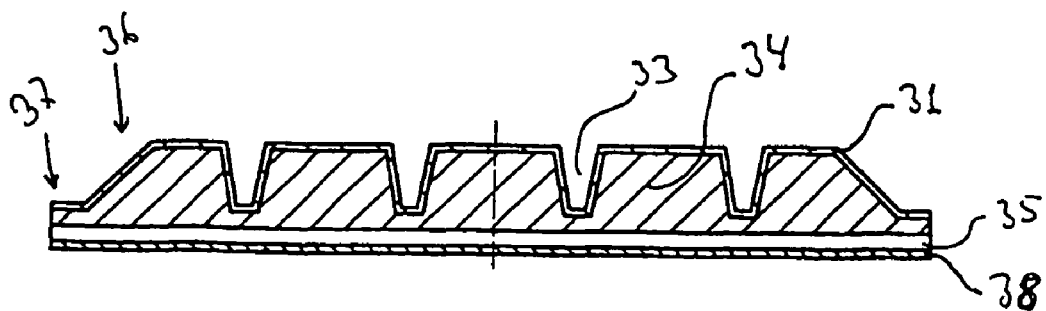
FIG. 7 shows in an enlarged scale a sectional view of the embodiment of FIG. 5 along the line A-A.
Figure 8:
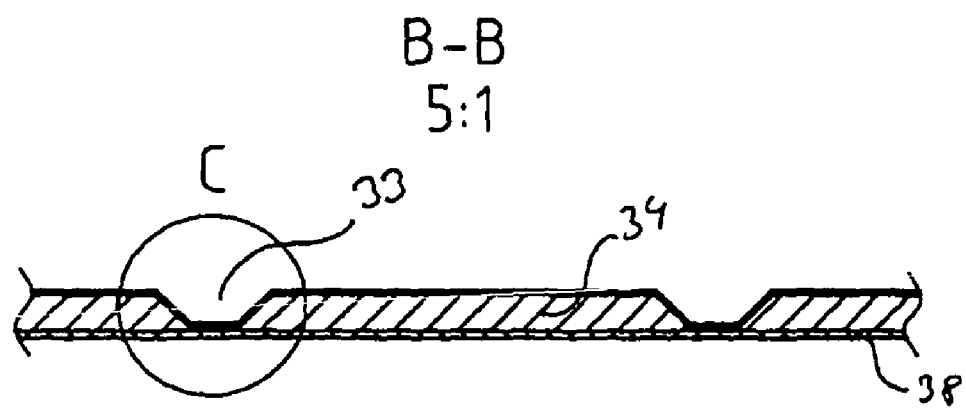
FIG. 8 shows in an enlarged scale a sectional view of the embodiment of FIG. 5 along the line B-B.
Figure 9:
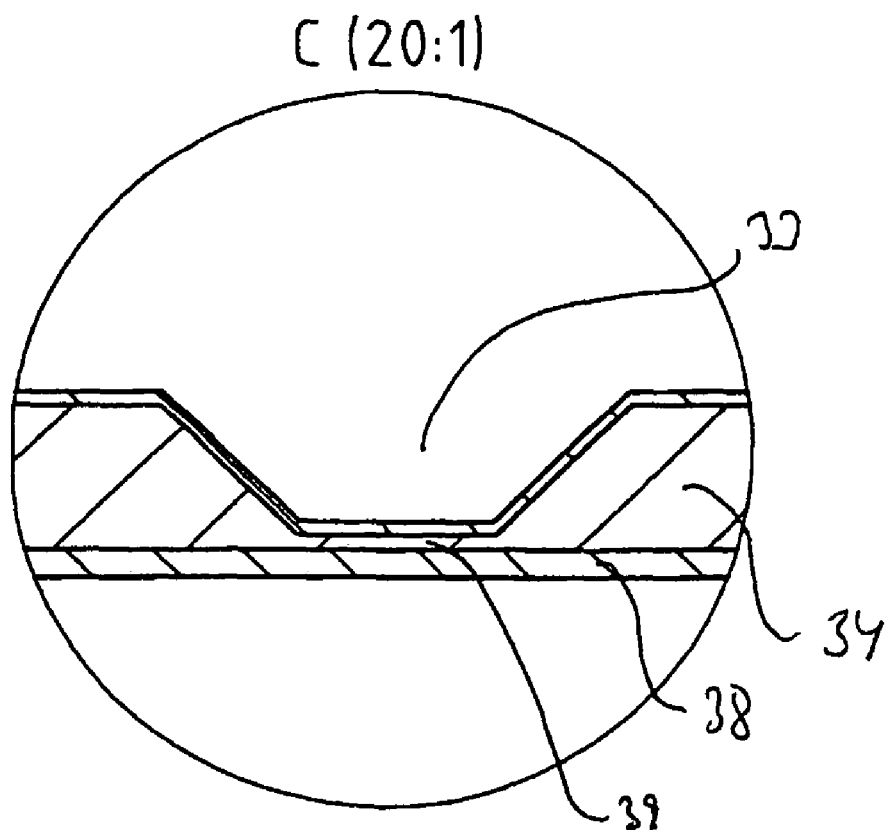
FIG. 9 shows in a further enlarged scale a detail in the area marked C in FIG. 8.

FIG. 7 shows in an enlarged scale a sectional view of the embodiment of FIGS. 5 and 6 along the line A-A, and more clearly showing the adhesive areas 34 having the maximum thickness of the dressing and the indentations 33. In this embodiment the indentations are wider at the top end and narrower at the bottom end. Furthermore, the rim is shown having a bevel 36 leaving a relatively thin edge 37. Furthermore, the top film layer 31 is shown as well as a release liner 38. Between the release-liner 38 and the adhesive 34 the fold 35 is seen. FIG. 8 shows in an enlarged scale a sectional view along the line B-B of the embodiment of FIG. 5 showing an adhesive areas 34 and two indentations 33 and FIG. 9 shows in a further enlarged scale a detail of the indentation area marked C in FIG. 8 showing and indentation 33 between two adhesive areas 34 and the release liner 38 and more clearly the thickness 39 of the dressing at the bottom of the indentations.

The invention is further elucidated and explained below in the working examples disclosing preparation and testing of embodiments of dressings according to the invention.

Example 1

Comparison of a Dressing of the Invention with Conventional Dressing on Elbow

Dressings of the invention were made from blanks comprising a backing layer and a layer of skin-friendly adhesive as disclosed in U.S. Pat. No. 4,367,732 using a press and using a mould made from aluminium and having a surface corresponding to the desired pattern of indentations. The width of the indentations was about 1 millimetre and the transverse measurement of the areas between the indentations was about 5 millimetres. The mould was then suitably closed using a pressure of up to 10-40 metric tons at a temperature of about 90-110° C. for 1-3 seconds. Controls were prepared using identical blanks but only impressing a bevelled edge.

In a preliminary test, dressings of the invention were tested on a volunteer for covering an elbow and compared with a corresponding dressing without indentations. The dressing of the invention showed a much longer wearing time of 10-12 days as opposed to about 4 days for the control.

The dressings were of the embodiment as shown in FIG. 4 and were tested on healthy volunteers in a screening test.

The dressings according to this invention showed an extended wear time when applied to the elbow or the knee as compared to the controls. The wear time of the dressings of the invention (A) was found to be clearly longer than the wear time of the controls (B). The results are summarized in the below Table 1 stating the percentage of dressings still being in service.

TABLE 1

| Time | Elbow | | Knee | |
| --- | --- | --- | --- | --- |
| Days | A | B | A | B |
| 1 | 100 | 100 | 100 | 100 |
| 8 | 30 | 0 | 40 | 20 |
| 11 | 20 | 0 | 10 | 0 |
| 14 | 0 | 0 | 10 | 0 |

It appears that the dressings of the invention show longer wear time that the controls for elbows and knees, most pronounced for elbows. Most test persons reported that the dressing of the invention was more elastic and flexible than the control.

Thus, a dressing of the invention provides prolonged wear time and a substantial better feeling for the user when the dressing is applied, which is believed to be ascribed to the great flexibility of the dressing allowing the dressing to follow all the movements of the user perfectly.

Also stress generated in the adhesive and the backing layer caused by movement while wearing is believed to be stopped by pattern of indentations and confined to a few of the adhesive areas having maximum thickness without propagating to the edge of the dressing and thus preventing a loosening of the dressing.

Also the applying of the dressing according to the invention on the parts of the body mentioned above is easier compared with a dressing according to the prior because of the flexing feature of the dressing.

Example 2

Test of Dressing not According to the Invention having Indentations in Adhesive Surface Facing the Skin to be Covered on Bend of Elbow Dressings corresponding to the dressing of the invention tested in Example 1 but having the indentations at the adhesive surface for contacting the skin instead of in the surface covered by the backing layer were prepared. The dressings were tested on two volunteers for covering the bend (cubital area) of an elbow and both test persons reported that the feeling was utmost uncomfortable due to pinching effects.

Example 3

Comparison of a Dressing of the Invention with Conventional Dressing on Palm of the Hand Dressings according to the invention as tested in Example 1 were tested on volunteers on the palm of the hand and compared to controls as in example 1.

In total 40 dressings were tested on 40 volunteers and the number of dressings staying in place after 24, 48, and 72 hours normal daily routine was recorded. The dressings according to this invention showed an extended wear time when applied to the palm of the hand as compared to the controls. The average wear time of the dressings of the invention (A) was found to be clearly longer than the wear time of the controls (B). The results are summarized in the below Table 2 stating number of dressings still being in service and show that the dressing according to the invention shows a longer average use time than a corresponding dressing without indentations.

TABLE 2

| Time Hours | Remaining Dressings | |
| --- | --- | --- |
| | A | B |
| 24 | 19 | 17 |
| 48 | 10 | 6 |
| 72 | 3 | 2 |
| Average use (Hrs) | 30 | 23 |

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A dressing comprising a backing layer and an adhesive layer, said adhesive layer being uninterrupted on a surface facing the skin and having on an opposite side facing away from the skin a pattern of connected indentations formed into the adhesive layer to provide a multiplicity of adjacent adhesive areas, said pattern of connected indentations comprising:
    a first indentation formed into the adhesive layer in a first direction, the first indentation parallel to a first line of multiple adhesive areas;
    a second indentation formed into the adhesive layer in a second direction that is different from the first direction, the second indentation parallel to a second line of multiple adhesive areas; and
    a third indentation formed into the adhesive layer in a third direction that is different from the first direction and the second direction, the third indentation parallel to a third line of multiple adhesive areas
    wherein the first, second, and third indentations increase flexibility of the dressing by allowing the dressing to bend in the first, second and third directions without bending two or more of the adhesive areas.

2. The dressing as claimed in claim 1, wherein at least one of the first, second, and third indentations has an indentation width that is broader than the remaining indentations.

3. The dressing as claimed in claim 2, wherein the indentation having the width that is broader than the remaining indentations follows an outer contour of said dressing to allow the user to customize a size of the dressing while retaining a shape corresponding to said outer contour.

4. The dressing as claimed in claim 1 wherein the first, second, and third indentations form of a symmetrical pattern of multiple adjacent adhesive areas.

5. The dressing as claimed in claim 1 wherein the first, second, and third indentations intersect.

6. The dressing as claimed in claim 1 wherein each of the adhesive areas is in the form of an essentially circular shape.

7. The dressing as claimed in claim 1 wherein the indentations have depth of at least two thirds of the total thickness of the dressing.

8. The dressing as claimed in claim 1 wherein a width of the indentations is from about 0.2 mm to about 3 mm and a size of adhesive areas between said indentations is from about 2 mm to about 25 mm.

9. The dressing as claimed in claim 1 wherein the backing layer is a substantially water-impervious film.

10. The dressing as claimed in claim 1 wherein the outer periphery of the dressing is bevelled such that the thickness adjacent to the edge does not exceed about 30% of the maximum thickness of the dressing.

11. The dressing as claimed in claim 1, wherein said pattern of connected indentations covers over half of a surface area of said dressing.

12. The dressing as claimed in claim 1, wherein said pattern of connected indentations covers substantially all of a surface area of said dressing.

13. The dressing as claimed in claim 1, wherein said pattern of indentations forms a plurality of adhesive areas that are separated from one another by said indentations, said plurality of adhesive areas arranged in one of a vertical, a horizontal or a diagonal sequence.

14. A dressing comprising:
    an adhesive layer applied to a backing layer and having an uninterrupted adhesive surface opposite the backing layer, the adhesive layer including a pattern of grooves formed into the adhesive layer to provide a multiplicity of adjacent adhesive islands, the pattern of grooves comprising a first groove aligned in a first direction, a second groove aligned in a second direction different than the first direction, and a third groove aligned in a third direction different than the first and second directions;
    wherein the grooves increase flexibility of the dressing by allowing the dressing to bend in the grooves in the first, second and third directions without bending two or more of the adhesive islands.

15. The dressing of claim 14, wherein the adhesive islands define areas of maximum thickness for the dressing.

16. The dressing of claim 14, wherein the pattern of grooves formed into the adhesive layer provide a multiplicity of circular adhesive islands.

17. The dressing of claim 14, wherein the pattern of grooves formed into the adhesive layer provide a multiplicity of adjacent and non-concentric adhesive islands.

* * * * *